(12) United States Patent
Suehara

(10) Patent No.: US 10,406,324 B2
(45) Date of Patent: Sep. 10, 2019

(54) ACTUATING MEMBER AND MEDICAL APPARATUS

(71) Applicant: Terumo Kabushiki Kaisha, Tokyo (JP)

(72) Inventor: Satoru Suehara, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 1042 days.

(21) Appl. No.: 14/184,395

(22) Filed: Feb. 19, 2014

(65) Prior Publication Data
US 2014/0249473 A1    Sep. 4, 2014

(30) Foreign Application Priority Data

Mar. 1, 2013  (JP) .................................. 2013-040964

(51) Int. Cl.
    *A61M 25/01*        (2006.01)
(52) U.S. Cl.
    CPC .............................. *A61M 25/0136* (2013.01)
(58) Field of Classification Search
    CPC ........ A61M 25/0147; A61M 2025/015; A61M 25/01; A61M 25/0105; A61M 25/0133; A61M 25/0136–0152; A61M 2025/0161; A61B 1/0051–1/01
    See application file for complete search history.

(56) References Cited

U.S. PATENT DOCUMENTS

| | | | | |
|---|---|---|---|---|
| 4,483,326 A | * | 11/1984 | Yamaka | A61B 1/0057 600/141 |
| 4,942,866 A | * | 7/1990 | Usami | A61B 1/0052 600/148 |
| 5,195,968 A | * | 3/1993 | Lundquist | A61M 25/0144 600/585 |
| 5,199,950 A | * | 4/1993 | Schmitt | A61M 25/0147 600/585 |
| 5,472,017 A | * | 12/1995 | Kovalcheck | A61B 1/0052 138/103 |
| 6,033,378 A | * | 3/2000 | Lundquist | A61M 25/0136 604/528 |
| 6,126,633 A | * | 10/2000 | Kaji | A61M 25/0084 604/164.01 |

(Continued)

FOREIGN PATENT DOCUMENTS

JP    2008-142199 A    6/2008

*Primary Examiner* — Bhisma Mehta
*Assistant Examiner* — Laura C Schell
(74) *Attorney, Agent, or Firm* — Foley & Lardner LLP

(57) ABSTRACT

An actuating member for making a flexible elongated member perform a predetermined action includes a push/pull member having a tip side and a base end side, the push/pull member including: a first moving portion and a second moving portion that are located on the base end side of the push/pull member and are movable relative to one another along an axis of the push/pull member, a first extending portion that extends from the first moving portion towards the tip side of the push/pull member, and a second extending portion that extends from the second moving portion towards the tip side of the push/pull member; an operating member that is rotatable about an axis that intersects an axis of the push/pull member, the operating member being configured such that rotation of the operating member causes movement of the first moving portion and the second moving portion.

6 Claims, 7 Drawing Sheets

(56) References Cited

U.S. PATENT DOCUMENTS

| | | | |
|---|---|---|---|
| 8,043,288 B2* | 10/2011 | Dando | A61B 18/1492 606/41 |
| 2004/0034348 A1* | 2/2004 | Rashidi | A61B 18/1492 606/41 |
| 2006/0142695 A1* | 6/2006 | Knudson | A61M 25/0136 604/95.04 |
| 2008/0139886 A1 | 6/2008 | Tatsuyama | |
| 2008/0161790 A1* | 7/2008 | Dando | A61B 18/1492 606/41 |
| 2010/0069834 A1* | 3/2010 | Schultz | A61M 25/0136 604/95.04 |
| 2011/0054287 A1* | 3/2011 | Schultz | A61B 5/0422 600/374 |
| 2012/0143088 A1* | 6/2012 | Schultz | A61B 5/6852 600/585 |
| 2013/0324973 A1* | 12/2013 | Reed | A61M 25/0136 604/528 |
| 2014/0058323 A1* | 2/2014 | Hoshino | A61B 1/0052 604/95.04 |
| 2014/0276222 A1* | 9/2014 | Tegg | A61M 25/0136 600/585 |
| 2015/0105809 A1* | 4/2015 | Connolly | A61M 25/0136 606/159 |

\* cited by examiner

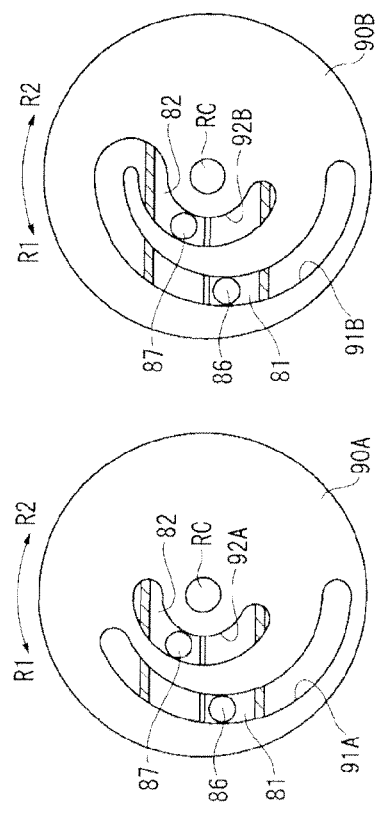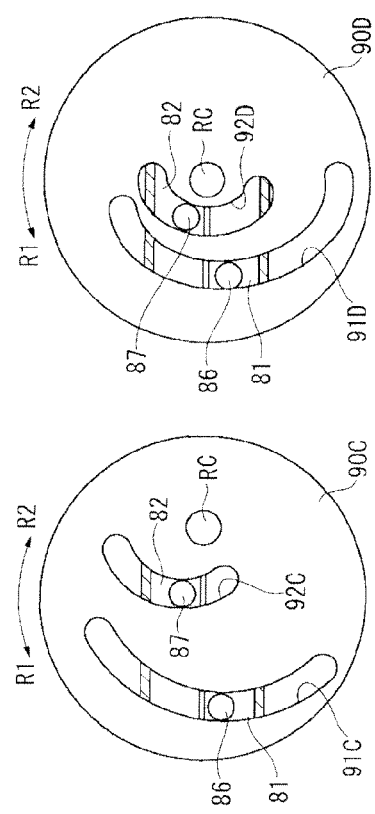

ACTUATING MEMBER AND MEDICAL APPARATUS

CROSS-REFERENCE TO RELATED APPLICATIONS

This application claims priority to and the benefit of Japanese Patent Application No. 2013-040964, filed Mar. 1, 2013, the entire contents of which are incorporated herein by reference.

BACKGROUND

The present disclosure relates to an actuating member for making a medical elongated member perform a predetermined action, and a medical apparatus equipped with the actuating member.

In the medical field, an elongated member having flexibility is generally used as a medical apparatus for access for performing administration of medicine into a living body, suction or injection of various fluids, introduction of other medical apparatus into the living body, or the like. For example, where an elongated member is used for introduction of other medical apparatus, prior to the introduction of the medical apparatus, the elongated member is inserted into a lumen (a blood vessel, a body cavity, or the like) of the living body, and is guided to a target area, such as an area to be treated and its peripheral area. In order to appropriately guide the elongated member to the target area in during such use, it is often necessary to introduce the elongated member along a curved path like the lumen of the living body. For this reason, the elongated member may include an actuating member capable of performing a bending operation by a user's proximal operation when the elongated member is used.

As techniques related to this, Japanese Patent Publication No. JP-A-2008-142199 describes an actuating member including a push/pull member connected to an elongated member, a pulley around which the push/pull member is wound, a handle for rotationally actuating the pulley, and an endoscope into which the actuating member is assembled. In this actuating member, the handle is arranged on a base end side of the endoscope and rotates around an axis orthogonal to the axial direction of the elongated member, thereby winding the push/pull member to perform a bending action.

In the actuating member of JP-A-2008-142199, the push/pull member is arranged so as to be wound around the pulley and an action direction in which the push/pull member is pushed/pulled is converted from a straight direction into a circumferential direction for bending. Therefore, a relatively rigid small wire or the like is used as the push/pull member. For this reason, there is a possibility that a push/pull force cannot be reliably transmitted to the elongated member via this wire.

Additionally, since it is necessary to wind the wire around the pulley with good followability, there are problems in that the pulley must be large, which causes the entire apparatus to be large.

SUMMARY

Embodiments of the present invention have been developed in order to solve the above problems. For example, one object of embodiments of the present invention is to provide an actuating member capable of efficiently transmitting the advance/retraction movement of a push/pull member to an elongated member and capable of achieving the miniaturization of an entire medical apparatus. Another object of embodiments of the present invention is to provide a medical apparatus equipped with such an actuating member.

The above object is achieved by the invention described in any one of the following (1) to (9).

(1) An actuating member for making a medical elongated member having flexibility perform a predetermined action including a push/pull member that includes a first moving portion and a second moving portion which are arranged on a base end side of the elongated member in an axial direction and are provided so as to be relatively movable along the axial direction of the elongated member, a first extending portion which extends from the first moving portion to a tip side of the elongated member in the axial direction, and a second extending portion which extends from the second moving portion to the tip side of the elongated member in the axial direction and that is pushed/pulled in the axial direction of the elongated member with the movement of the first moving portion and the second moving portion; and an operating member that is provided so as to be rotatable with an axis in a direction intersecting the axial direction of the elongated member as a rotation center and operates the movement of the first moving portion and the second moving portion. At least one of the first and second moving portions and the operating member is provided with a first guide groove that guides the movement of the first moving portion and a second guide groove that guides the movement of the second moving portion. The push/pull member transmits the movement of the first moving portion and the second moving portion by the first guide groove and the second guide groove to the elongated member to thereby enable the elongated member to perform at least one action of an advance/retraction action and a bending action.

(2) The actuating member according to the above (1) in which the operating member is configured so as to be capable of moving the first moving portion and the second moving portion, respectively, in opposite directions along the axial direction, and the bending action of the elongated member is performed by moving the first moving portion and the second moving portion.

(3) The actuating member according to the above (1) in which the operating member is configured so as to be capable of moving the first moving portion and the second moving portion with different traveling distances, respectively, in the same direction along the axial direction, and the advance/retraction action and bending action of the elongated member is performed by moving the first moving portion and the second moving portion.

(4) The actuating member according to any one of the above (1) to (3) in which the operating member is constituted by a disk-shaped member in which the first guide groove that engages a first projection provided on the first moving portion and the second guide groove that engages a second projection provided on the second moving portion are formed in a disk surface, and is provided so that the movement of the first moving portion and the second moving portion is operable by rotating the operating member.

(5) The actuating member according to the above (4) in which the first guide groove and the second guide groove are provided at positions where the guide grooves sandwich the rotation center.

(6) The actuating member according to the above (4) in which the first guide groove and the second guide groove are provided on the same side with respect to the rotation center.

(7) The actuating member according to any one of the above (1) to (6) in which the operating member is provided so as to be rotatable with an axis orthogonal to the axis of the elongated member as a rotation center.

(8) The actuating member according to any one of the above (1) to (7) further including a visual recognition portion that enables the traveling distances of the first moving portion and the second moving portion to be confirmed by visual recognition.

(9) A medical apparatus including the actuating member according to any one of the above (1) to (8), and an elongated member having flexibility that performs at least one action of an advance/retraction action and a bending action by the actuating member.

According to the embodiment described in the above (1), the push/pull member is pushed/pulled in the axial direction of the elongated member without conversion of its action direction, and thereby makes the elongated member perform an advance/retraction action or a bending action. Therefore, the advance/retraction movement of the push/pull member can be efficiently transmitted to the elongated member. Additionally, since it is not necessary to wind the push/pull member around the operating member, the miniaturization of a whole medical apparatus can be achieved.

According to the embodiment described in the above (2), since the bending action of the elongated member is performed by moving the first moving portion and the second moving portion in opposite directions, the elongated member can be bent with shorter traveling distances of the first moving portion and the second moving portion, and the operativity of the actuating member is improved.

According to the embodiment described in the above (3), since the bending action of the elongated member is performed by moving the first moving portion and the second moving portion in the same direction, the elongated member can be made to perform the bending action while being made to perform the advance/retraction action, and a higher-performance actuating member can be provided.

According to the embodiment described in the above (4), since the respective moving portions are moved by making the projections of the first and second moving portions engage the first and second guide grooves, the elongated member can be bent with a simple configuration, and a medical apparatus can be further miniaturized.

According to the embodiment described in the above (5), since the first guide groove and the second guide groove are provided at positions where the guide grooves sandwich the rotation center of the operating member, large spaces for forming the respective guide grooves can be made, and the degree of freedom in arrangement of the first guide groove and the second guide groove can be enhanced.

According to the embodiment described in the above (6), since the first guide groove and the second guide groove are provided on the same side with respect to the rotation center of the operating member, the operating member can be made small and the medical apparatus can be further miniaturized.

According to the embodiment described in the above (7), since the operating member is provided so as to be rotatable with the axis orthogonal to the axis of the elongated member as a rotation center, it is not necessary to offset the operating member with respect to the elongated member, and further miniaturization of a medical apparatus can be achieved.

According to the embodiment described in the above (8), since the traveling distances of the first moving portion and the second moving portion can be confirmed by the visual recognition portion, the operativity of the actuating member is improved.

According to the embodiment described in the above (9), it is possible to provide a medical apparatus equipped with the actuating member that can efficiently transmit the advance/retraction movement of the push/pull member to the elongated member and can achieve the miniaturization of the whole apparatus.

BRIEF DESCRIPTION OF DRAWINGS

FIG. 7A is a plan view showing an operating member of the medical apparatus according to a first modification.

FIG. 7B is a plan view showing an operating member of the medical apparatus according to a second modification.

FIG. 7C is a plan view showing an operating member of the medical apparatus according to a third modification.

FIG. 7D is a plan view showing an operating member of the medical apparatus according to a fourth modification.

DETAILED DESCRIPTION

Hereinafter, embodiments of the invention will be described with reference to the drawings. In addition, for convenience of description, dimension scales of the drawings may be exaggerated and be different from actual scales. Additionally, in the following description, a proximal operation side of a medical apparatus related to each embodiment of the invention is referred to as a "base end side", and a side where insertion into a living body lumen is made is referred to as a "tip side".

First Embodiment

The configuration of a medical apparatus 1 related to a first embodiment of the invention will be described.

Figure 1:
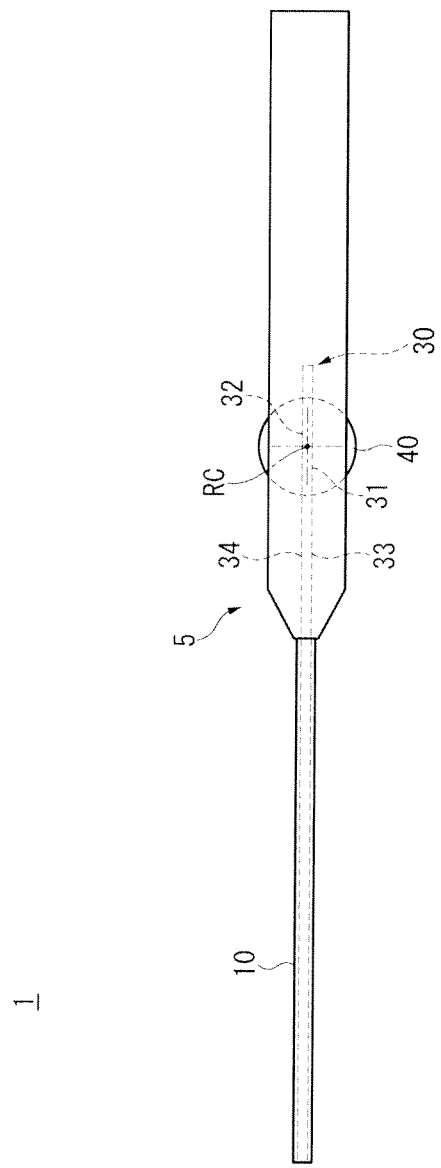
FIG. 1 is a schematic configuration view showing a medical apparatus related to a first embodiment of the invention.
Figure 2:
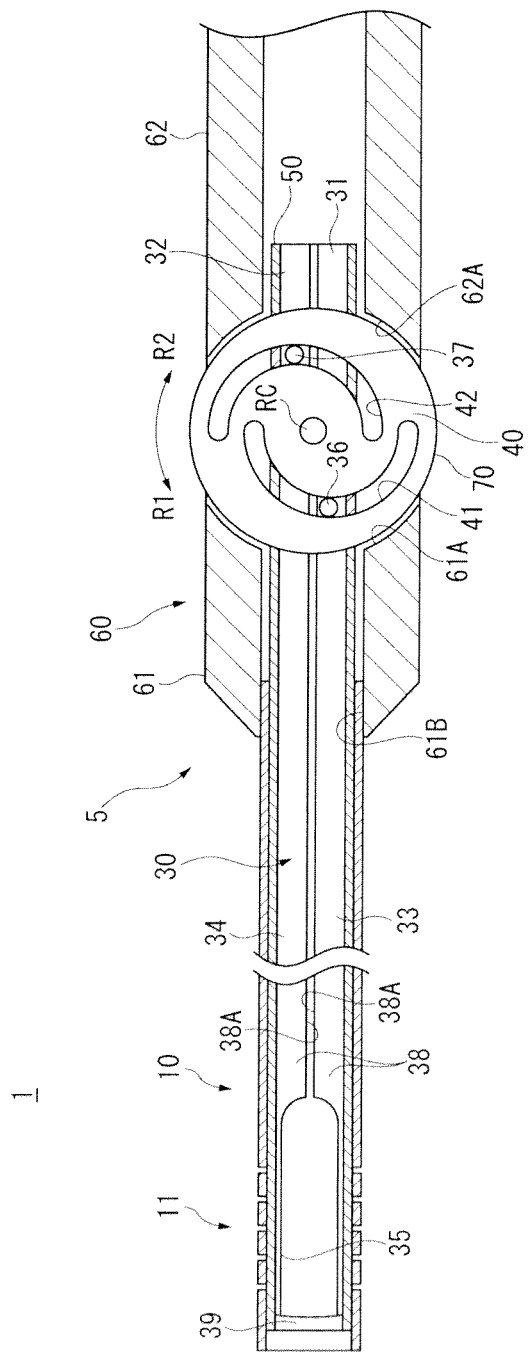
FIG. 2 is a side cross-sectional view showing the medical apparatus related to the first embodiment.

FIG. 1 is a schematic configuration view showing the medical apparatus 1 related to the first embodiment of the invention. FIG. 2 is a side cross-sectional view showing the medical apparatus 1 related to the first embodiment.

If the medical apparatus 1 related to the first embodiment of the invention is outlined, as shown in FIG. 1, the medical apparatus includes a medical elongated member 10 having flexibility, and an actuating member 5 for making the elongated member 10 perform a predetermined action. The actuating member 5 includes a first moving portion 31 and a second moving portion 32 that are arranged on the base end side of the elongated member 10 in the axial direction and are provided so as to be relatively movable along the axial direction of the elongated member 10, a first extending portion 33 that extends from the first moving portion 31 to the tip side of the elongated member 10 in the axial direction, and a second extending portion 34 that extends from the second moving portion 32 to the tip side of the elongated member 10 in the axial direction, and has a push/pull member 30 that is pushed/pulled in the axial direction of the elongated member 10 with the movement of the first moving portion 31 and the second moving portion 32. Additionally, the actuating member 5 further has an operating member 40 that is rotatably provided using an axis in a direction intersecting the axial direction of the elongated member 10 as a rotation center RC to operate the movement of the first moving portion 31 and the second moving portion 32. The operating member 40 is provided with a first guide groove 41 that guides the movement of the first moving portion 31, and a second guide groove 42 (FIG. 2) that guides the movement of the second moving portion 32, and the push/pull member 30 is able to transmit the movement of the first moving portion 31 and the second moving portion 32 by the first guide groove 41 and the second guide groove 42 to the elongated member 10 to thereby make the elongated member 10 perform a bending action. Hereinafter, detailed description will be made.

The actuating member 5, as shown in FIG. 2, has the push/pull member 30 that is pushed/pulled in the axial direction of the elongated member 10 with the movement of the first moving portion 31 and the second moving portion 32, the operating member 40 for operating the movement of the first moving portion 31 and the second moving portion 32, a sealing portion 50 that is provided at an outer periphery of the push/pull member 30 to seal a fluid that flows through the inside of the push/pull member 30, a base portion 60 that is provided at the outer periphery of the sealing portion 50 on the base end side to support the push/pull member 30 and the operating member 40, and a visual recognition portion 70 that enables the traveling distances of the first moving portion 31 and the second moving portion 32 to be confirmed by visual recognition.

Figure 3:
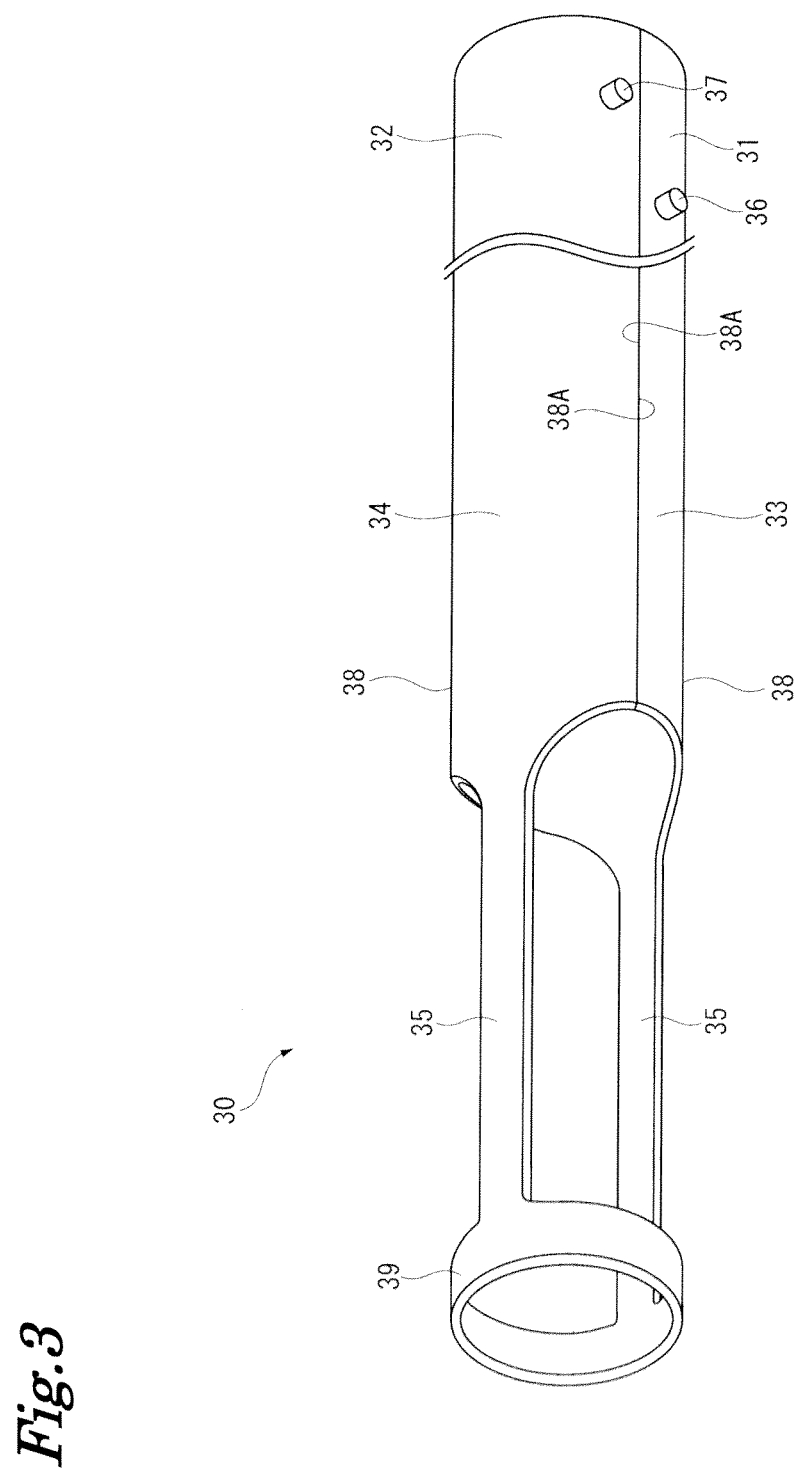
FIG. 3 is a perspective view showing a push/pull member.

FIG. 3 is a perspective view showing the push/pull member 30.

The push/pull member 30, as shown also in FIG. 3, includes a plurality of divided portions 38 that are divided in the circumferential direction to form a tubular structure, and an annular connecting portion 39 that connects the tips of the respective divided portions 38 in the axial direction, and the divided portions 38 are pushed/pulled in the axial direction of the elongated member 10 with the movement of the first moving portion 31 and the second moving portion 32 to thereby make the elongated member 10 perform a bending action.

The divided portions 38 include the first moving portion 31 and the second moving portion 32 that are arranged on the base end side of the elongated member 10 in the axial direction and are provided so as to be relatively movable along the axial direction of the elongated member 10, the first extending portion 33 that extends from the first moving portion 31 to the tip side of the elongated member 10 in the axial direction, the second extending portion 34 that extends from the second moving portion 32 to the tip side of the elongated member 10 in the axial direction, and bending portions 35 that are provided on tip sides of the first extending portion 33 and the second extending portion 34 and are bent by relatively pushing/pulling the first extending portion 33 and the second extending portion 34. In addition, the push/pull member 30 may be configured so as to be capable of pushing/pulling the tip side of the elongated member 10, and may be, for example, a pulling wire, a plate-shaped belt member, or the like.

The first moving portion 31 has a first projection 36 that protrudes in a direction parallel to divided surfaces 38A of the divided portions 38. The first projection 36 is provided further toward the tip side than the rotation center RC of the operating member 40 in a state where the bending portions 35 are not bent.

The second moving portion 32 has a second projection 37 that protrudes in a direction that is parallel to the divided surfaces 38A of the divided portions 38 and is the same as the protruding direction of the first projection 36. The second projection 37 is provided further toward the base end side (further toward the base end side than the first projection 36) than the rotation center RC of the operating member 40 in a state where the bending portions 35 are not bent.

The first extending portion 33 transmits the movement of the first moving portion 31 to the bending portions 35.

The second extending portion 34 transmits the movement of the second moving portion 32 to the bending portions 35.

The bending portions 35, which are portions formed as circumferential end edges of the divided portions 38 on the tip sides thereof are cut out, are formed so as to be narrower than the first extending portion 33 and the second extending portion 34.

Since the push/pull member 30 has the above configuration, the bending portions 35 are bent upward when the first extending portion 33 is arranged further toward the tip side than the second extending portion 34 by the above-described movement, and on the contrary, the bending portions 35 are bent downward when the first extending portion 33 is arranged further toward the base end side than the second extending portion 34.

The operating member 40 is configured so as to be capable of moving the first moving portion 31 and the second moving portion 32, respectively, in opposite directions along the axial direction, and the bending action of the elongated member 10 is performed by moving the first moving portion 31 and the second moving portion 32. Additionally, the operating member 40 is constituted by a disk-shaped member in which the first guide groove 41 as a guide groove that engages the first projection 36 provided on the first moving portion 31 and the second guide groove 42 as a guide groove that engages the second projection 37 provided on the second moving portion 32 are formed in a disk surface, and is provided so that the movement of the first moving portion 31 and the second moving portion 32 is operable by rotating the operating member 40. Additionally, the operating member 40 makes the first moving portion 31 and the second moving portion 32 relatively move to approach each other with the rotation thereof, and bends the elongated member 10. Additionally, since the operating member 40 has irregularities (not shown) provided on an outer peripheral surface thereof, the operating member has a shape such that the operating member is rotatable by operator's fingers.

The first guide groove 41 and the second guide groove 42 are formed in the shape of a semicircular arc of a true circle, respectively, and are provided at positions where the guide grooves sandwich the rotation center RC with the inner sides of the semicircular arcs being directed to the rotation center RC of the operating member 40.

The center of curvature of the first guide groove 41 is provided at a position apart from the rotation center RC toward the end portion of the first guide groove 41 in the direction of R1. Also, the first guide groove 41 is formed in a shape such that the end portion thereof in the direction of R2 is provided at a position closer to the rotation center RC than the end portion thereof in the direction of R1 and the distance from the rotation center RC increases gradually toward the direction of R1. In other words, a radial distance between the center axis of rotation RC of the operating member 40 and the first end portion of the first guide groove 41 is greater than a radial distance between the center axis of rotation RC of the operating member 40 and the second end portion of the first guide groove 41. That is, the first guide groove 41 is formed so that the first moving portion 31 is moved to the tip side of the elongated member 10 when the operating member 40 is rotated in the direction of R2 and the first moving portion 31 is moved to the base end side when the operating member 40 is rotated in the direction of R1.

The center of curvature of the second guide groove 42 is provided at a position apart from the rotation center RC toward the end portion (opposite side of the center of curvature of the first guide groove 41) of the second guide groove 42 in the direction of R1. Also, the second guide groove 42 is formed in a shape such that the end portion thereof in the direction of R2 is provided at a position closer to the rotation center RC than the end portion thereof in the direction of R1 and the distance from the rotation center RC increases gradually toward the direction of R1. In other words, a radial distance between the center axis of rotation RC of the operating member 40 and the second end portion of the second guide groove 42 is greater than a radial distance between the center axis of rotation RC of the operating member 40 and the first end portion of the second guide groove 42. That is, the second guide groove 42 is formed so that the second moving portion 32 is moved to the base end side of the elongated member 10 when the operating member 40 is rotated in the direction of R2 and the second moving portion 32 is moved to the tip side when the operating member 40 is rotated in the direction of R1.

The sealing portion 50 seals the fluid that flows through the inside of the push/pull member 30. The sealing portion 50 is brought into close contact with and fixed to the outer periphery of the push/pull member 30. The fixing method is not particularly limited, and the sealing portion can be fixed by, for example, an adhesive, brazing, fusing, or the like. The materials that constitute the sealing portion 50 are, for example, fluororesins such as ETFE (ethylene tetrafluoro ethylene copolymer) and PTFE (polytetrafluoroethylene), and polyolefins such as PE (polyethylene) and PP (polypropylene), and thermoplastic resins such as polyamide, polyester, and polyurethane, which are excellent in biocompatibility. In addition, the sealing portion 50 may be arranged inside the push/pull member 30.

The base portion 60 supports the elongated member 10, the push/pull member 30, and the operating member 40. The base portion 60 has a supporting portion 61 that is arranged further toward the tip side than the operating member 40 to support the elongated member 10, the push/pull member 30, and the operating member 40, and a gripping portion 62 that is arranged further toward the base end side than the operating member 40, supports the push/pull member 30 and the operating member 40, and is gripped by an operator when the operator performs a procedure. The base portion 60 is made of for example, a rigid resin material.

The supporting portion 61 supports the elongated member 10, the push/pull member 30, and the operating member 40. The supporting portion 61 has a recessed portion 61A that is provided on the base end side to house the operating member 40, and an opening portion 61B that is provided on the tip side to allow the elongated member 10 to be inserted therethrough.

The gripping portion 62 supports the push/pull member 30 and the operating member 40 and is gripped by an operator when the operator performs a procedure. The gripping portion 62 has a recessed portion 62A that is provided on the tip side to house the operating member 40.

The visual recognition portion 70 is provided on the disk surface or outer peripheral surface of the operating member 40, and enables the traveling distances of the first moving portion 31 and the second moving portion 32 to be confirmed by visual recognition. Although the visual recognition portion 70 is, for example, a marker, the visual recognition portion is not limited to this and may be a scale or the like.

The tip side of the elongated member 10 is bent as the base end side of the elongated member is inserted into the opening portion 61B and the bending portions 35 are bent. The elongated member 10 has a rigidity weakened portion 11 capable of being easily bent, on the tip side thereof. In the present embodiment, the rigidity weakened portion 11 has a configuration in which metallic tubular members used for an endoscope or the like are combined. Although the rigidity weakened portions 11 are provided in two places in the up-and-down direction, the rigidity weakened portion may be provided in at least one place. In addition, the elongated member 10 may be made of, for example, fluororesins such as ETFE (ethylene tetrafluoro ethylene copolymer) and PTFE (polytetrafluoroethylene), and polyolefins such as PE (polyethylene) and PP (polypropylene), and thermoplastic resins such as polyamide, polyester, and polyurethane, which are excellent in biocompatibility. In this case, although the rigidity weakened portion 11 is, for example, a slit, the rigidity weakened portion is not limited to this and a material having a lower rigidity than other portions may be used for the rigidity weakened portion 11.

Figure 4:
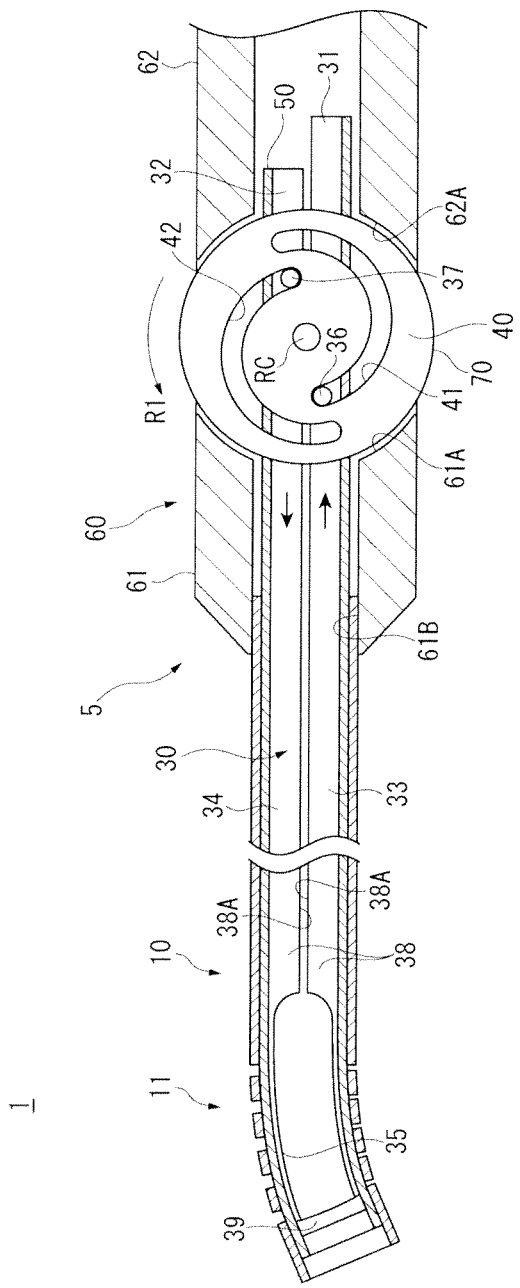
FIG. 4 is a side cross-sectional view showing the medical apparatus when a tip side of an elongated member is bent downward, in the first embodiment.

Next, a method of bending the elongated member 10 by the actuating member 5 related to the first embodiment of the invention will be described with reference to FIG. 4. FIG. 4 is a side cross-sectional view showing the medical apparatus 1 when the tip side of the elongated member 10 is bent downward.

An operator, as shown in FIG. 4, rotates the operating member 40 in the direction of R1. Then, the first moving portion 31 moves to the base end side as the first projection 36 is guided by the first guide groove 41, and moves the second moving portion 32 to the tip side as the second projection 37 is guided by the second guide groove 42. This allows the first extending portion 33 to be moved to the base end side and allows the second extending portion 34 to be moved to the tip side. If the first extending portion 33 is moved to the base end side and the second extending portion 34 is moved to the tip side, the bending portions 35 are bent downward. If the bending portions 35 are bent downward, the tip side of the elongated member 10 is bent downward.

As described above, according to the first embodiment of the invention, the push/pull member 30 is pushed/pulled in the axial direction of the elongated member 10 without conversion of its action direction, and thereby makes the elongated member 10 perform a bending action. Therefore, the advance/retraction movement of the push/pull member 30 can be efficiently transmitted to the elongated member 10. Additionally, since it is not necessary to wind the push/pull member 30 around the operating member 40, the miniaturization of the whole medical apparatus 1 can be achieved.

Additionally, the operating member 40 is configured so as to be capable of moving the first moving portion 31 and the second moving portion 32, respectively, in opposite directions along the axial direction, and the bending action of the elongated member 10 is performed by moving the first moving portion 31 and the second moving portion 32. For this reason, the elongated member 10 can be bent with shorter traveling distances of the first moving portion 31 and the second moving portion 32, and the operativity of the actuating member 5 is improved.

Additionally, since the respective moving portions 31 and 32 are moved by making the respective projections 36 and 37 of the first and second moving portions 31 and 32 engage the first and second guide grooves 41 and 42, the elongated member 10 can be bent with a simple configuration, and the medical apparatus 1 can be further miniaturized.

Additionally, since the first guide groove 41 and the second guide groove 42 are provided at positions where the guide grooves sandwich the rotation center RC of the operating member 40, large spaces for forming the respective guide grooves 41 and 42 can be made, and the degree of freedom in arrangement of the first guide groove 41 and the second guide groove 42 can be enhanced.

Additionally, the visual recognition portion 70 that enables the traveling distances of the first moving portion 31 and the second moving portion 32 to be confirmed by visual recognition is further included. For this reason, the traveling distances of the first moving portion 31 and the second moving portion 32 can be confirmed by the visual recognition portion 70, and the operativity of the actuating member 5 is improved.

Additionally, it is possible to provide the medical apparatus 1 equipped with the actuating member 5 that can efficiently transmit the advance/retraction movement of the push/pull member 30 to the elongated member 10 and can achieve the miniaturization of the whole apparatus.

Second Embodiment

Next, a second embodiment of the invention will be described. Description of portions that are common to those of the first embodiment will be omitted, and portions that have features only in the second embodiment will be described.

Figure 5:
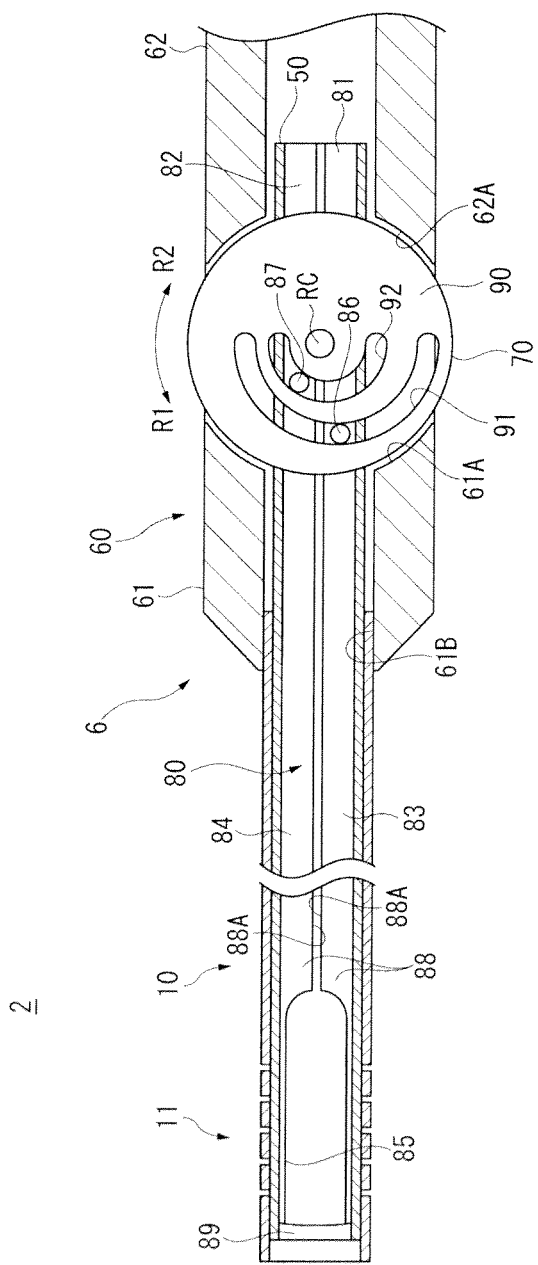
FIG. 5 is a side cross-sectional view showing a medical apparatus related to a second embodiment of the invention.

FIG. 5 is a side cross-sectional view showing a medical apparatus 2 related to the second embodiment of the invention.

The medical apparatus 2 related to the second embodiment of the invention, as shown in FIG. 5, has an actuating member 6, and the actuating member 6 has a push/pull member 80 that is pushed/pulled in the axial direction of the elongated member 10 with the movement of a first ng portion 81 and a second moving portion 82, and an operating member 90 for operating the movement of the first moving portion 81 and the second moving portion 82. In addition, the other configurations are the same as those of the first embodiment.

The push pull member 80 includes a plurality of divided portions 88 that are divided in the circumferential direction to form a tubular structure, and an annular connecting portion 89 that connects the tips of the respective divided portions 88 in the axial direction.

The divided portions 88 include the first moving portion 81 and the second moving portion 82 that are arranged on the base end side of the elongated member 10 in the axial direction and are provided so as to be relatively movable along the axial direction of an elongated member 10, a first extending portion 83 that extends from the first moving portion 81 to the tip side of the elongated member 10 in the axial direction, a second extending portion 84 that extends from the second moving portion 82 to the tip side of the elongated member 10 in the axial direction, and bending portions 85 that are provided on tip sides of the first extending portion 83 and the second extending portion 84 and are bent by relatively pushing/pulling the first extending portion 83 and the second extending portion 84.

The first moving portion 81 has a first projection 86 that protrudes in a direction parallel to divided surfaces 88A of the divided portions 88. The first projection 86 is provided further toward the tip side than the rotation center RC of the operating member 90 in a state where the bending portions 85 are not bent.

The second moving portion 82 has a second projection 87 that protrudes in a direction that is parallel to the divided surfaces 88A of the divided portions 88 and is the same as the protruding direction of the first projection 86. The second projection 87 is provided further toward the tip end side than the rotation center RC of the operating member 90 and further toward the base end side than the first projection 86 in a state where the bending portions 85 are not bent.

The operating member 90 is configured so as to be capable of moving the first moving portion 81 and the second moving portion 82 with different traveling distances, respectively, in the same direction along the axial direction, and the advance/retraction action and bending action of the elongated member 10 are performed by moving the first moving portion 81 and the second moving portion 82. Additionally, the operating member 90 is constituted by a disk-shaped member in which a first guide groove 91 as a guide groove that engages the first projection 86 provided on the first moving portion 81 and a second guide groove 92 as a guide groove that engages the second projection 87 provided on the second moving portion 82 are formed in a disk surface, and is provided so that the movement of the first moving portion 81 and the second moving portion 82 is operable by rotating the operating member 90. Additionally, the operating member 90 makes the first moving portion 81 and the second moving portion 82 relatively move to separate from each other with the rotation thereof, and bends the elongated member 10.

The first guide groove 91 and the second guide groove 92 are formed in the shape of a semicircular arc of a true circle, respectively, and are provided on the same side with respect to the rotation center RC with the inner sides of the semicircular arcs being directed to the rotation center RC of the operating member 90. Additionally, the first guide groove 91 is provided outside the second guide groove 92 and the centers of curvature of the guide grooves are provided at positions apart in the same direction (toward the end portions of the respective guide grooves 91 and 92 in the direction of R1) from the rotation center RC, respectively. Here, the center of curvature of the first guide groove 91 is located apart from the center of curvature of the second guide groove 92.

The first guide groove 91 is formed in a shape such that the end portion thereof in the direction of R2 is provided at a position closer to the rotation center RC than the end portion thereof in the direction of R1 and the distance from the rotation center RC increases gradually toward the direction of R1. That is, the first guide groove 91 is formed so that the first moving portion 81 is moved to the tip end side of the elongated member 10 when the operating member 90 is rotated in the direction of R2 and the first moving portion 81 is moved to the base end side when the operating member 90 is rotated in the direction of R1.

The second guide groove 92 is formed in a shape such that the end portion thereof in the direction of R2 is provided at a position closer to the rotation center RC than the end portion thereof in the direction of R1 and the distance from the rotation center RC increases gradually toward the direction of R1. That is, the second guide groove 92 is formed so that the second moving portion 82 is moved to the tip side of the elongated member 10 when the operating member 90 is rotated in the direction of R2 and the second moving portion 82 is moved to the base end side when the operating member 90 is rotated in the direction of R1.

Figure 6:
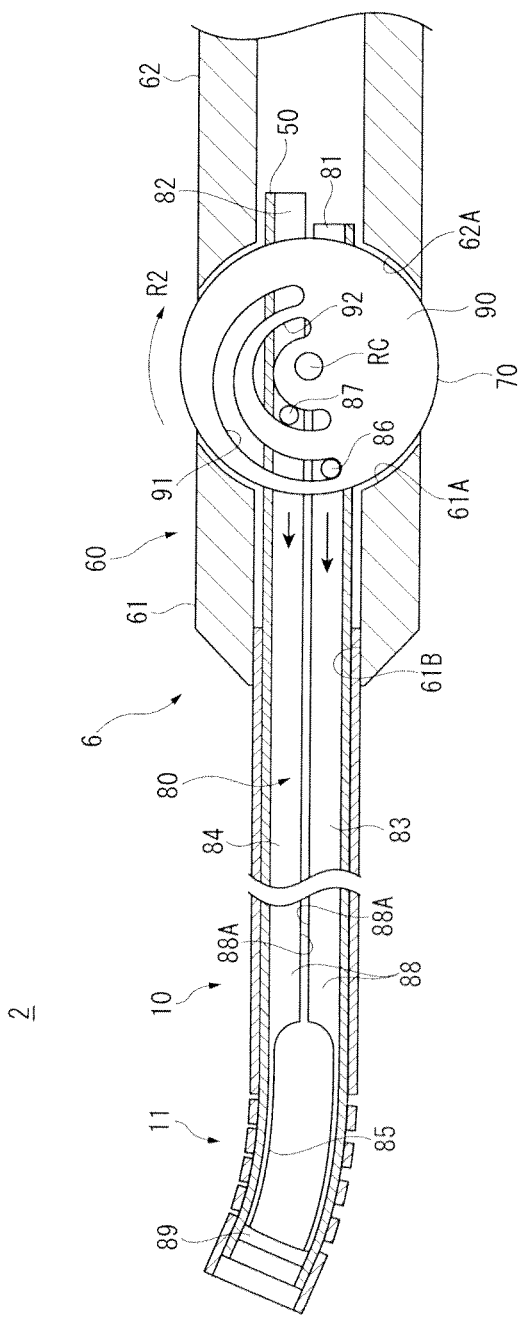
FIG. 6 is a side cross-sectional view showing the medical apparatus when a tip side of an elongated member is bent upward, in the second embodiment.

Next, a method of bending the tip side of the elongated member 10 by the actuating member 6 related to the second embodiment of the invention will be described with reference to FIG. 6. FIG. 6 is a side cross-sectional view showing the medical apparatus 2 when the tip side of the elongated member 10 is bent upward.

An operator, as shown in FIG. 6, rotates the operating member 90 in the direction of R2. Then, the first moving portion 81 is guided by the first guide groove 91 and is moved to the tip side, and the second moving portion 82 is also guided by the second guide groove 92 and is moved to the tip side. At this time, since the first guide groove 91 is formed so that the center of curvature thereof is provided at a position further apart from the rotation center RC than the center of curvature of the second guide groove 92 and the spacing from the second guide groove 92 increase toward the direction of R1, the first moving portion 81 moves further toward the tip side than the second moving portion 82. For this reason, the bending portions 85 are bent upward while being moved to the tip side. If the bending portions 85 are bent upward while being moved to the tip side, the tip side of the elongated member 10 is bent upward while the elongated member 10 is moved to the tip side.

As described above, according to the second embodiment of the invention, the push/pull member 80 is pushed/pulled in the axial direction of the elongated member 10 without conversion of its action direction, and thereby makes the elongated member 10 perform an advance/retraction action and a bending action. Therefore, the advance/retraction movement of the push/pull member 80 can be efficiently transmitted to the elongated member 10. Additionally, since it is not necessary to wind the push/pull member 80 around the operating member 90, the miniaturization of the whole medical apparatus 2 can be achieved.

Additionally, the operating member 90 is configured so as to be capable of moving the first moving portion 81 and the second moving portion 82 with different traveling distances, respectively, in the same direction along the axial direction, and the advance/retraction action and bending action of the elongated member 10 is performed by moving the first moving portion 81 and the second moving portion 82. For this reason, a higher-performance actuating member 6 can be provided.

Additionally, since the first guide groove 91 and the second guide groove 92 are provided on the same side with respect to the rotation center RC of the operating member 90, the operating member 90 can be made small and the medical apparatus 2 can be further miniaturized.

Hereinafter, modified examples of the above-described embodiments are illustrated.

FIGS. 7A to 7D are perspective views showing operating members 90A to 90D of the medical apparatus related to (Modification Example 1) to (Modification Example 4). In addition, components other than the operating members 90A to 90D are omitted in FIGS. 7A to 7D.

Modification Example 1

In the operating member 90A of the medical apparatus shown in FIG. 7A, a first guide groove 91A and a second guide groove 92A are formed in the shape of a circular arc of a true circle, respectively, and are provided on the same side with respect to the rotation center RC with the inner sides of the circular arcs being directed to the rotation center RC of the operating member 90A.

The first guide groove 91A is provided outside the second guide groove 92A and the center of curvature thereof is provided at a position apart from the rotation center RC toward the end portion of the first guide groove 91A in the direction of R1. Additionally, the first guide groove 91A is formed in a shape such that the end portion thereof in the direction of R2 is provided at a position closer to the rotation center RC than the end portion thereof in the direction of R1 and the distance from the rotation center RC increases gradually toward the direction of R1.

The second guide groove 92A is formed in a shape such that the curvature radius thereof is provided at almost the same position as the rotation center RC and the distance from the rotation center RC becomes constant.

According to this configuration, if the operating member 90A is rotated in the direction of R1, the second moving portion 82 does not move to the tip or base end side, and only the first moving portion 81 moves to the base end side. Since this allows the first extending portion 83 to move to the base end side, the bending portions 85 are bent downward and the tip side of the elongated member 10 is bent downward. On the other hand, since the second moving portion 82 does not move and only the first moving portion 81 moves to the tip side if the operating member 90 is rotated in the direction of R2, the bending portions 85 are bent upward and the tip side of the elongated member 10 is bent upward.

Modification Example 2

The operating member 90B of the medical apparatus shown in FIG. 7B is configured similar to the operating member 90A of (Modification Example 1) except that the end portions of a first guide groove 91B and a second guide groove 92B in the direction of R2 are formed continuously with each other.

According to this configuration, when the operating member 90B is rotated, the elongated member 10 is bent as in the case of (Modification Example 1). Additionally, since the first guide groove 91B and the second guide groove 92B are continuously formed, the processing when the respective guide grooves 91B and 92B are formed becomes easy, and the manufacturing efficiency of the medical apparatus can be improved.

Modification Example 3

The rotation center RC of an operating member 90C of the medical apparatus shown in FIG. 7C is eccentric with respect to the center of the operating member 90C. In the operating member 90C, a first guide groove 91C and a second guide groove 92C are formed in the shape of a circular arc of a true circle, respectively, and are provided on the same side with respect to the rotation center RC with the inner sides of the circular arcs being directed to the rotation center RC.

The first guide groove 91C is provided outside the second guide groove 92C and the center of curvature thereof is provided at a position apart from the rotation center RC toward the end portion of the first guide groove 91C in the direction of R1 and the tip side of the elongated member 10. Additionally, the first guide groove 91C is formed in a shape such that the end portion thereof in the direction of R2 is provided at a position closer to the rotation center RC than the end portion thereof in the direction of R1 and the distance from the rotation center RC increases gradually toward the direction of R1.

The second guide groove 92C is formed in a shape such that the end portion thereof in the direction of R1 is provided at a position closer to the rotation center RC than the end portion thereof in the direction of R2 and the distance from the rotation center RC decreases gradually toward the direction of R1.

According to this configuration, since the first moving portion 81 moves to the base end side and the second moving portion 82 moves to the tip side if the operating member 90C is rotated in the direction of R1, the tip side of the elongated member 10 is bent downward. On the other hand, since the first moving portion 81 moves to the tip side and the second moving portion 82 moves to the base end side if the operating member 90 is rotated in the direction of R2, the tip side of the elongated member 10 is bent upward.

Additionally, since the rotation center RC of the operating member 90C is eccentric, compared to a case where the rotation center RC is located at the center of the operating member 90C, the rotating speeds of the respective guide grooves 91C and 92C with respect to the rotating speed of the operating member 90C can be increased, and a bending action can be performed with a smaller amount of operation. Additionally, the shapes of the respective guide grooves 91C and 92C can be lengthened, and operation sensitivity can be enhanced by making shape changes fine.

Modification Example 4

In an operating member 90D of the medical apparatus shown in FIG. 7D, a first guide groove 91D and a second guide groove 92D are formed in the shape of a circular arc of a non-true circle, for example, an ellipse, respectively, and are provided on the same side with respect to the rotation center RC with the inner sides of the circular arcs being directed to the rotation center RC of the operating member 90D. Also, the first guide groove 91D and the second guide groove 92D are formed in a shape such that the curvature radii vary depending on positions, respectively, and the distances from the rotation center RC increase or decrease from one end toward the other end.

According to this configuration, since the first moving portion 81 moves to the base end side and the second moving portion 82 moves to the tip side if the operating member 90D is rotated in the direction of R1, the tip side of the elongated member 10 is bent downward. On the other hand, since the first moving portion 81 moves to the tip side and the second moving portion 82 moves to the base end side if the operating member 90 is rotated in the direction of R2, the tip side of the elongated member 10 is bent upward.

Additionally, since the traveling distances of the respective moving portions 81 and 82 can be changed depending on the rotational position of the operating member 90D, the speed at which the elongated member 10 is bent during the rotation of the operating member 90D can be changed.

In addition, the invention is not limited to the aforementioned embodiment or the aforementioned modification examples, and alternations, improvements, or the like within the scope that the object of the invention can be achieved will be included in the invention.

For example, the first guide groove may be provided in the first moving portion 31, 81, the second guide groove may be provided in the second moving portion 32, 82, and the first projection and the second projection may be provided on the operating member 40, 90. Additionally the first guide groove may be provided in the first moving portion 31, 81, the second projection may be provided on the second moving portion 32, 82, the first projection and the second guide groove may be provided in the operating member 40, 90, or its reverse combination may be adopted.

Moreover, arbitrary shapes may be adopted as the shapes of the first guide groove 41, 91, 91A to 91D and the second guide groove 42, 92, 92A to 92D so long as the first moving portion 31, 81 and the second moving portion 32, 82 are relatively movable along the axial direction of the elongated member 10. For example, a shape such that the outer side of a circular arc is directed to the rotation center RC of the operating member 40, 90, 90A to 90D may be adopted, or a linear shape may be adopted.

Additionally, the first projection 36, 86 and the second projection 37, 87 may be provided on the first moving portion 31, 81 and the second moving portion 32, 82 via additional members, or the first projection 36, 86, the second projection 37, 87 and the rotation center RC may be arranged so as to coincide with each other on a major axis of the elongated member 10. Additionally, the rotation center RC that intersects an axis of the push/pull member may be arranged so as to be offset from the axis of the push/pull member.

Additionally, the first guide groove 41, 91, 91A to 91D and the second guide groove 42, 92, 92A to 92D may not pass through the operating member 40, 90, 90A to 90D, and may be formed in a concave shape.

The push/pull member 30, 80 may not include the connecting portion 39, 89. In this case, for example, if each extending portion 33, 34, 83, 84 is connected to the elongated member 10, the elongated member 10 can be bent.

Additionally, bendable arbitrary configurations can be used for the elongated member 10.

What is claimed is:

1. An actuating member for making a flexible elongated member perform a predetermined action, the actuating member comprising:
 a push/pull member having a tip side and a base end side, the push/pull member including:
  a first moving portion and a second moving portion that are located on the base end side of the push/pull member and are movable relative to one another along an axis of the push/pull member, the first moving portion comprising a first projection, and the second moving portion comprising a second projection,
  a first extending portion that extends from the first moving portion towards the tip side of the push/pull member, and
  a second extending portion that extends from the second moving portion towards the tip side of the push/pull member;
 an operating member that is rotatable about a center axis of rotation that intersects the axis of the push/pull member, the operating member being configured such that rotation of the operating member causes movement of the first moving portion and the second moving portion,
 wherein the operating member includes a disk-shaped member that includes:
  a first guide groove that is engaged with the first projection of the first moving portion so as to guide movement of the first moving portion, and
  a second guide groove that is engaged with the second projection of the second moving portion so as to guide movement of the second moving portion, wherein the push/pull member is configured to transmit the movement of the first moving portion and the second moving portion to the flexible elongated member via the first extending portion and the second extending portion, to thereby enable the flexible elongated member to perform at least one of (i) an advance/retraction action, and (ii) a bending action, wherein each of the first guide groove and the second guide groove includes a first end portion and a second end portion, wherein a radial distance between the center axis of rotation of the operating member and the first end portion of the first guide groove is greater than a radial distance between the center axis of rotation of the operating member and the second end portion of the first guide groove, wherein a radial distance between the center axis of rotation of the operating member and the second end portion of the second guide groove is greater than a radial distance between the center axis of rotation of the operating member and the first end portion of the second guide groove, wherein each of the first guide groove and the second guide groove is formed in a shape of a semicircular arc, and wherein in the first guide groove and the second guide groove, each respective first end portion is located on a first side of the center axis of rotation of the operating member, and each respective second end portion is located on a second side of the center axis of rotation of the operating member, such that the center axis of rotation of the operating member is located between each respective first end portion and each respective second end portion along a diameter of the operating member.

2. The actuating member according to claim 1, wherein the operating member is configured to cause the movement of the first moving portion and the second moving portion, respectively, in opposite directions along the axis of the push/pull member, and the push/pull member is configured to transmit the movement of the first moving portion and the second moving portion to the elongated member via the first extending portion and the second extending portion, to thereby enable the elongated member to perform the bending action.

3. The actuating member according to claim 1, wherein the first guide groove and the second guide groove are disposed on opposite sides of the center axis of rotation of the operating member.

4. The actuating member according to claim 1, wherein the center axis of rotation of the operating member is perpendicular to the axis of the push/pull member.

5. The actuating member according to claim 1, further comprising a visual recognition portion that enables traveling distances of the first moving portion and the second moving portion to be confirmed by visual recognition.

6. A medical apparatus comprising:
a flexible elongated member; and
an actuating member for making the flexible elongated member perform a predetermined action, the actuating member comprising:
a push/pull member having a tip side and a base end side, the push/pull member including:
a first moving portion and a second moving portion that are located on the base end side of the push/pull member and are movable relative to one another along an axis of the push/pull member, the first moving portion comprising a first projection, and the second moving portion comprising a second projection,
a first extending portion that extends from the first moving portion towards the tip side of the push/pull member, and
a second extending portion that extends from the second moving portion towards the tip side of the push/pull member;
an operating member that is rotatable about a center axis of rotation that intersects the axis of the push/pull member, the operating member being configured such that rotation of the operating member causes movement of the first moving portion and the second moving portion,
wherein the operating member includes a disk-shaped member that includes:
a first guide groove that is engaged with the first projection of the first moving portion so as to guide movement of the first moving portion, and
a second guide groove that is engaged with the second projection of the second moving portion so as to guide movement of the second moving portion,
wherein the push/pull member is configured to transmit the movement of the first moving portion and the second moving portion to the flexible elongated member via the first extending portion and the second extending portion, to thereby enable the flexible elongated member to perform at least one of (i) an advance/retraction action, and (ii) a bending action,
wherein each of the first guide groove and the second guide groove includes a first end portion and a second end portion,
wherein a radial distance between the center axis of rotation of the operating member and the first end portion of the first guide groove is greater than a radial distance between the center axis of rotation of the operating member and the second end portion of the first guide groove,
wherein a radial distance between the center axis of rotation of the operating member and the second end portion of the second guide groove is greater than a radial distance between the center axis of rotation of the operating member and the first end portion of the second guide groove,
wherein each of the first guide groove and the second guide groove is formed in a shape of a semicircular arc, and
wherein in each of the first guide groove and the second guide groove, each respective first end portion is located on a first side of the center axis of rotation of the operating member, and each respective second end portion is located on a second side of the center axis of rotation of the operating member, such that the center axis of rotation of the operating member is located between each respective first end portion and each respective second end portion along a diameter of the operating member.

* * * * *